United States Patent [19]
Soldani

[11] Patent Number: 5,387,621
[45] Date of Patent: Feb. 7, 1995

[54] POROUS MEMBRANES BASED ON UNSTABLE POLYMER SOLUTIONS

[75] Inventor: Giorgio Soldani, Pisa, Italy

[73] Assignee: Kontron Instruments, Inc., Everett, Mass.

[21] Appl. No.: 16,516

[22] Filed: Feb. 11, 1993

Related U.S. Application Data

[62] Division of Ser. No. 761,508, Sep. 18, 1991, Pat. No. 5,229,045.

[51] Int. Cl.$^6$ ............................................. C08J 9/28
[52] U.S. Cl. ................................. 521/155; 521/60; 521/64; 521/184; 536/3; 536/55.1; 536/56
[58] Field of Search ............... 521/155, 60, 64, 184; 536/3, 55.1, 56

[56] References Cited

U.S. PATENT DOCUMENTS

| | | | |
|---|---|---|---|
| 3,968,292 | 7/1976 | Pearman et al. | 521/63 |
| 3,982,335 | 9/1976 | Cunningham et al. | 521/61 |
| 4,127,124 | 11/1978 | Clagett et al. | 521/159 |
| 4,661,530 | 4/1987 | Gogolewski et al. | 521/137 |
| 4,914,064 | 4/1990 | Schucker | 521/159 |
| 5,063,186 | 11/1991 | Schucker | 521/159 |
| 5,208,313 | 5/1993 | Krishan | 521/154 |

*Primary Examiner*—Morton Foelak
*Attorney, Agent, or Firm*—Morgan & Finnegan

[57] ABSTRACT

Porous, distensible, gel-like membranes which in tubular form are suitable as implants, e.g., vascular prostheses and a process for the preparation thereof is described. The membranes are formed by a spraying, phase-inversion technique which employs thermodynamically unstable polymer solutions and is accomplished by separately spraying the unstable solution and a nonsolvent onto a rotating surface. Prostheses from the highly porous tubular membranes have shown a high degree of patency and completeness of the healing process and are useful for direct implantation in the body or for extracorporeal vascular accesses.

15 Claims, 2 Drawing Sheets

POROUS MEMBRANES BASED ON UNSTABLE POLYMER SOLUTIONS

This is a continuation of co-pending application Ser. No. 07/761,508 filed Sep. 18, 1991, now U.S. Pat. No. 5,229,045.

BACKGROUND AND FIELD OF THE INVENTION

The present invention relates to the provision of a prosthesis material for use with a living body, the material possessing biocompatibility and blood compatibility. The invention includes a method for the manufacture of such material.

Vascular prostheses made of porous fabrics such as expanded polytetrafluoroethylene (Teflon ®) and woven or knitted polyethyleneterephthalate (Dacron ®), although successful in the replacement of large-diameter arteries, have not proven useful for long-term applications as venous or small-diameter arterial substitutes.

Numerous techniques have been described in the prior art to produce porous or filamentous small-diameter tubular fabrics from polymers. For example, White and co-workers in Science, 1972, 176, pages 922-924 and Arch Surg., 1979, 114, page 698 reported a replamineform template process using calcite derived from sea urchin spines. The spines were machined into tubes of the desired diameter and wall thickness and then pressure-injected with a polyurethane solution. Following solvent evaporation, the calcite was dissolved with hydrochloric acid, leaving a polymer wall structure with interconnected pores. Lyman et al. in Trans. Am. Soc. Artif. Intern. Organs, 1977, 23, pages 253-260 reported a technique for producing porous, compliant prostheses using repeated cycles of dipping a glass mandrel in a copolyetherurethane-urea using N,N-dimethylformamide (DMF) as a solvent, and precipitation in water. Annis et al. in Trans. Am. Soc. Artif. Intern. Organs, 1978, 24, pages 209-213 reported the preparation of filamentous polyurethane tubes by electrostatic spinning. In this process, a highly porous and distensible non-woven fabric was formed by ejecting a polymer solution from a syringe onto a sliding, rotating steel mandrel through an electrostatic field obtained by maintaining the mandrel at −20 kV. Leidner et al. in J. Biomed. Mater. Res., 1983, 17, pages 229-247 disclosed the extrusion of a polymer in the liquid phase (either melted or dissolved in a solvent) through fine orifices to form fibers which could be stretched and wound onto a rotating mandrel. Prosthesis material has also been produced by a method wherein: 1) a polymer solution in a mixed solvent is formed by bringing a polymer solution near its precipitation point by the addition of a nonsolvent; 2) a substrate is coated with this so-form solution and 3) a porous structure is formed by evaporating at least part of the solvent fraction of the mixed solvent. (See Gogolewski et al, PCT published application WO86/0204, International Application No. PCT/SE85/00420, published on May 22, 1986). Recently, Kowligi et al. in J. Biomed. Mater. Res., 1988, 22 A3, pages 245-256 described a spraying technique to apply a fine mixture of polymer solution and nitrogen gas bubbles onto a rotating mandrel.

It is an object of the present invention to provide a new and flexible approach for the fabrication of membranes, especially tubular membranes, suitable as prostheses, especially vascular prostheses, most especially a small diameter vascular prosthesis.

It is further object of the present invention to provide a small diameter highly porous tubular membrane vascular prostheses which shows a high degree of patency and which does not induce anastomotic hyperplasia.

A still further object of the present invention is to provide a highly porous membrane prostheses, especially in small diameter tubular form, which promotes minimal connective tissue growth on the luminal surface to support the formation of a thin, stable, mature neointima and which enhances completeness of the healing process.

A yet further object of the present invention is to provide a process for the preparation of porous membranes which is relatively simple, flexible and reproducible.

BRIEF DESCRIPTION OF THE INVENTION

Figure 1:
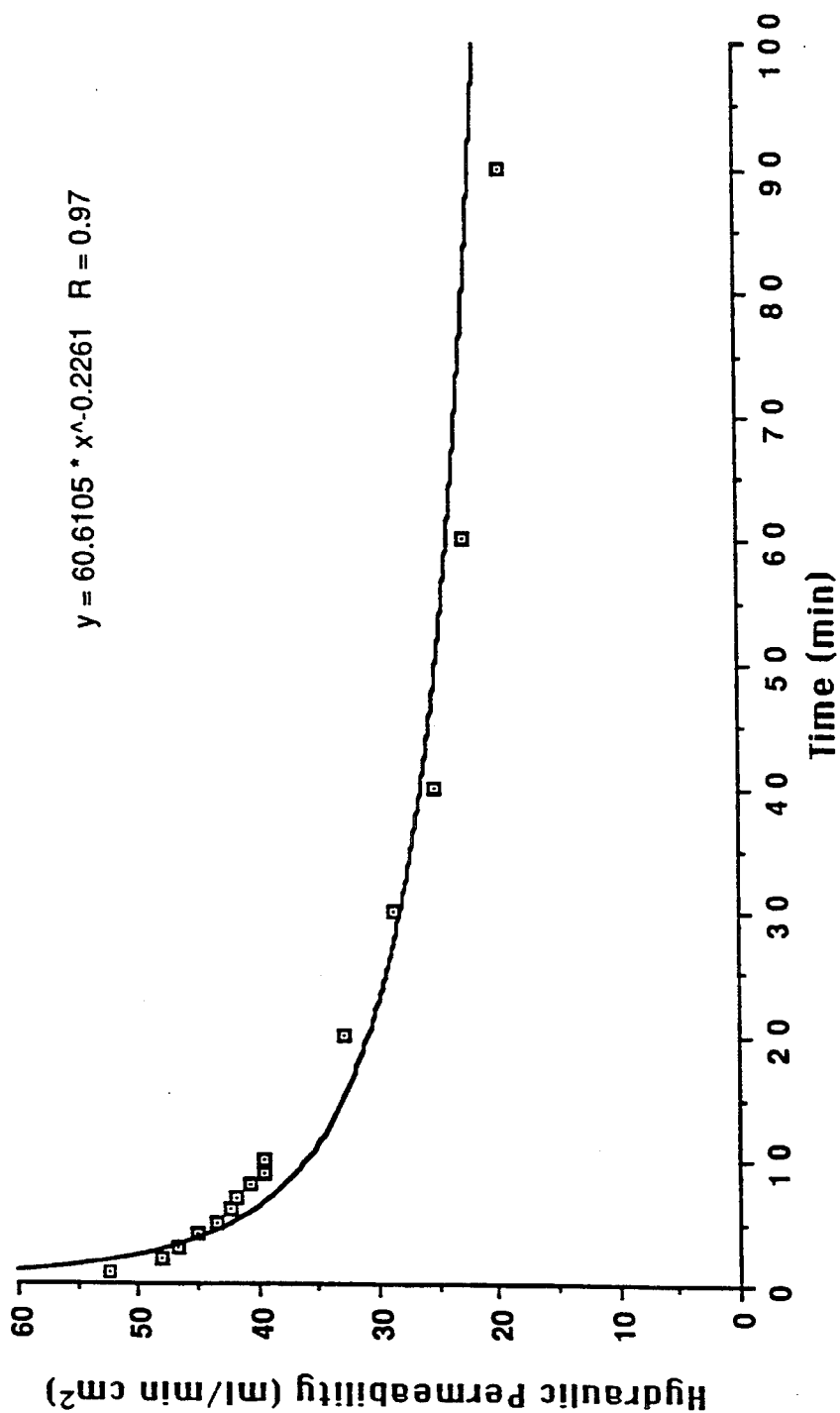
FIG. 1 is a plot of hydraulic permeability versus time.

A process is disclosed for the preparation of porous membranes utilizing a spraying, phase-inversion technique. Gel-like membranes are obtained from thermodynamically unstable polymer solutions. The unstable solution is provided by the careful addition of a nonsolvent to a dilute polymer solution and membranes are obtained by the simultaneous but separate spraying of the unstable polymer solution and nonsolvent for the unstable solution from a separate spray means onto a sliding and rotating mandrel. The present gel-like tubular membranes obtained by the phase-inversion effect derived from the local precipitation of a thermodynamically unstable polyurethane-polydimethylsiloxane solution have a spongy communicating porous cell wall structure with a filamentous outer and inner surface.

The highly porous tubular membranes of the present invention formed from polyurethane-polydimethylsiloxane solutions have been examined by scanning electron microscopy (SEM) and been shown to possess: 1) a filamentous inner surface with interfiber spacing ranging from about 30 to 150 $\mu$m in size, preferably 50 to 150 $\mu$m and most preferably 90 to 150 $\mu$m; 2) a spongy communicating porous cell wall structure; 3) a filamentous outer surface with interfiber spacing of from about 30 to 150 $\mu$m, preferably 50 to 150 $\mu$m and most preferably 90 to 150 $\mu$m; 4) a hydraulic permeability measured collecting, in the first minute, from 30 to 60 ml min$^{-1}$cm$^{-2}$; and 5) a high water content. Using the method of the present invention small diameter vascular prostheses which can achieve clinically acceptable patency rates when used in a diameter of less than 8 mm (I.D.) can be produced. Such prostheses can be employed for the replacement of coronary or distal peripheral arteries or as a channel which can support a complete recovery of nerve function and as a clinically acceptable bioartificial organ. A flat membrane can be produced by longitudinally cutting the tubular membrane formed on the mandrel and opening the cut cylinder into a flat position.

DETAILED DESCRIPTION OF THE INVENTION

The present invention utilizes a technique which can be described as "spraying-phase inversion". This process produces permeable or semi-permeable tubular membranes through the deposition of thin layers of a synthetic polymer onto a rotating mandrel. The apparatus which can be used to carry out the present process comprises a precision lathe in which mandrels of different diameters can be rotated using an electronically controlled variable speed motor. Adjacent to the lathe bed is positioned a carriage which can move bidirectionally and in parallel with the rotating mandrel of the lathe. This carriage is driven by an electronically controlled motor which can be automatically reversed by the action of electromechanical relays controlled by microswitches. Two spray means, e.g., spray guns, are mounted on the carriage and can be fixed at different angles to one another, and at different distances between the spray gun nozzles and the lathe mandrel. In this way, the streams from the spray means can be directed onto precise points along the lathe mandrel surface.

Using the above-described apparatus, an unstable polymer solution and a nonsolvent for the polymer can be simultaneously but separately sprayed from the two spray means at about the same volumetric flux onto rotating lathe mandrels of varying diameters.

After a number a passes of the streams from the spray means onto the rotating mandrel, tubular membranes of varying thicknesses and porosity ranges are produced. The degree of porosity of the membrane can be varied by adding different amounts of nonsolvents or by using nonsolvents of differing chemical compositions to the polymeric solution. The mandrel rotation speed and carriage movement speed can be set to predetermined values and both the nonsolvent and polymer solution can be sprayed at predetermined pressures, angles and distances between spray gun nozzles and mandrel.

If so desired, semipermeable tubular membranes having a dense skin on the inner surface and/or outer surface of the membrane can be produced. The skin layer can be obtained by depositing dense layers of polymer onto the rotating mandrel using a single spray means, i.e., without using the second spray means containing the non-solvent. Using this single spray technique, a material having a skin on either the inner or outer surface or both the inner and outer surfaces of the membrane can be produced. Membranes with a molecular weight cut-off in a range varying from about 10,000 to 70,000 Daltons can be produced by varying the thickness of the skin layer in the range of from about 2 to 10 μm. Segments of such membranes might be employed, for example, to produce macrocapsules for immuno-protected cells transplantation.

Various combinations of parameters related to the spraying, phase-inversion technique can be used to fabricate porous membranes using thermodynamically unstable polymer solutions. The preferred limits over which these parameters can vary in preparing highly porous small diameter tubular membranes are given in Table I, below.

TABLE I

| | |
|---|---|
| 1. Polymer solution concentration (% w/v) | 0.1–5.0 |
| 2. Nonsolvent added to the polymer solution (% v/v) | 1–50 |
| 3. Gas driving pressure (p.s.i.) | 1–45 |
| 4. Polymer solution flow rate (ml/min) | 0.5–5.0 |
| 5. Nonsolvent flow rate (ml/min) | 0.5–5.0 |
| 6. Angle between spray gun(s) and mandrel (°) | 70–80 |
| 7. Distance between nozzles and mandrel (mm) | 15–100 |
| 8. Mandrel diameter (prosthesis ID) (mm) | 0.5–1000 |
| 9. Mandrel rotation speed (r.p.m.) | 100–2000 |

TABLE I-continued

| | |
|---|---|
| 10. Carriage movement speed (cm/min) | 10–500 |
| 11. Internal nozzles bore (mm) | 0.2–0.5 |

The wall thickness of the tubular membrane produced is related to the volume of polymer solution sprayed. When a desired end point reached, the process can be stopped and the mandrel, preferably made of or coated with teflon, having the deposited material thereon was submerged overnight in a bath of nonsolvent in order to cure the delicate sponge-like structure of the membrane by allowing exchange of the solvent system for the nonsolvent. The finished membrane, if to be used in cylindrical form, can be removed from the mandrel by reducing the sleeve diameter through axial stretching of the mandrel. If a flat membrane is being prepared, a preferred means of removing the material is to longitudinally slit or cut the cylindrical structure on the mandrel and opening the membrane into a flat structure. The membrane can be left in nonsolvent or, preferably, distilled water at room temperature until needed for use.

A major advantage of the present technique as compared to prior art methods is its flexibility. By varying the amount of nonsolvent in the polymer solution and adjusting the parameters of the spinning process, the porosity of the membrane can be varied over a wide range. As a result, tubular membranes with wall compliance values ranging from venous to arterial to rather rigid tube properties can be attained.

The highly porous membranes of the present invention have the surprising property of being highly porous but having a low hydraulic permeability. As can be seen from the plot shown in FIG. 1, the hydraulic permeability of a highly porous membrane according to the present invention decreases over time in a manner dependent upon pressure in a test which measures degassed water passing through the membrane wall under 120 mm Hg.

The present porous membranes are prepared from thermodynamically unstable solutions of polymers. The polymer can be natural or synthetic. Examples of the former are polyamino-acids (e.g. polyglycin), polysaccharides (e.g. cellulose derivatives, alginates). Examples of synthetic polymers are silicones and polyurethanes. Mixtures of various polymers can also be used. A new class of materials known as fluorinated polyurethanes can also be employed. Additionally, copolyurethanes, particularly, block or segmented copolyurethane may be employed. Polymers useful in the present invention should have good elastomeric properties as well as being biocompatible and blood compatible. It is especially desirable that the polymer have good solubility and stability in relatively low boiling point, water-miscible solvents.

As a solvent, there may be used any solvent having the ability to dissolve the polymer used, but preferred solvents are those selected from the group consisting of tetrahydrofuran, amide solvents and sulfoxide solvents and dioxanes. Examples of such solvents are: tetrahydrofuran (THF), 1;4-dioxane, dimethylacetamide (DMAC), dimethylformamide (DMF), dimethylsulfoxide (DMSO), etc.

A useful class of polymers, namely the preferred polyurethane-polysiloxanes is disclosed in U.S. Pat. No. 3,562,352, and an especially useful group of such materials are the polyether urethane-poly(dialkylsiloxanes), most desirably a polyether urethane-polydimethylsiloxane. An example of such a material is Cardiothane 51 ® sold by Kontron Instruments, Inc., Everett, Mass. which is a blend of about 90% polyurethane and about 10% polydimethylsiloxane.

Segmented aliphatic polyrethanes or segmented aromatic polyurethanes may be used in order to obtain materials which are non-toxic, non-mutagenic and, non-carcinogenic it is preferred to use segmented aliphatic polyurethanes or using another expression aliphatic block copolymers.

The polymeric material for use in the invention may be conventionally prepared from aliphatic polyurethanes based on diisocyanates, e.g. 1,2-diisocyanatoethane, 1,5-diisocyanato pentane, hexamethylene diisocyanate, methane diisocyanato pentane, 1,9-diisocyanato nonane, 1,8-diisocyanato octane, 1,4-diisocyanato butane, 4,4'-methylenebiscyclohexyl diisocyanate, lysine diisocyanate, 1,4-transcyclohexane diisocyanate, dimethyldiisocyanato silane, diethyldiisocyanato silane. In addition to such diisocyanates there may be used polyols having average molecular weight within the range of 500 to 10000, e.g. poly(ethylene adipate), poly(tetra-methylene adipate), poly(1,4-cyclohexyldimethylene adipate), poly-(hexamethylene oxalate), poly(hexamethylene glutarate), poly($\epsilon$-caprolactone), poly(tetramethylene oxide), poly(ethylene oxide), poly(1,2-propylene oxide). Chain extenders e.g. 1,4-butandiol, 2,4,6-tris(dimethylaminomethyl)-phenol glycerol, 3,6-dioxactane 1-8-diol, ethylene diol, diethylene diol, tetramethylene diamine, ethylene diamine, hexamethylene diamine, propylene diamine.

The copolyurethanes are conventionally formed by e.g. reacting a prepolymer such as a polyether diol, with a diisocyanate, and the product resulting from such reaction may then be chain extended by reacting with a diol or diamide.

The preferred solvent system for the polyurethanepolydimethylsiloxane solutions is a mixture of THF and 1,4-dioxane, preferably a 2:1 mixture.

With respect to the nonsolvent, any solvent which is miscible with the solution solvent and has a solubility parameter different from the polymer can be used. Without wishing to be limited, examples of possible nonsolvents which might be mentioned are water, alcohol and water containing substances which enhance the inducement of solution instability and/or precipitation of the polymer from solution. It is preferred that the nonsolvent be relatively low boiling. Preferred nonsolvents are water, lower alkanols, such as ethanol, and mixtures of water and a lower alkanol.

Preparation of a thermodynamically unstable solution is done by selecting a nonsolvent, i.e., liquid miscible with the solution solvent and having a solubility parameter different from the polymer, and titrating the polymer solution with the nonsolvent to determine the point at which incompatibility is visually detectable by the appearance of turbidity or actual polymer precipitation. In the preferred system, titration is conducted to determine the amount of nonsolvent necessary to allow solution to remain clear but at which precipitation would occur with the addition of a small amount of nonsolvent. The nonsolvent tolerance of the polymer solution can be estimated by placing 100 ml of polymer solution in a vessel maintained at room temperature (25° C.) under gentle stirring and then, using a digital titration burette, slowly adding nonsolvent to the solution until incompatibility is usually detectable.

To fabricate the present membranes, a precision lathe is used in which mandrels of different diameters could be rotated at speeds from 0 to 5000 rpm using an electronically controlled variable speed motor. Parallel to the axis of the lathe a carriage was positioned which can move bidirectionally along the axis of the rotating mandrel which was powered by a motor and which can be automatically reversed by the action of electromechanical relays controlled by micro-switches. Two spray means in the form of modified spray guns can be mounted horizontally on the carriage and positioned so the centerline of the nozzles of the modified spray guns and the mandrel lay in the same plane. The distance and angle between the mandrel and the modified spray gun nozzles was adjusted so that the intersection of the jets from the nozzles occurred at the surface of the mandrel. The mixing chamber of each modified spray gun was equipped with two ports, one connected to a 100 ml glass reservoir for the unstable polymer solution or the nonsolvent (precipitating fluid), the other connected to a compressed nitrogen tank equipped with a flow regulator and a pressure gauge.

To fabricate a membrane, the reservoirs of the modified spray guns were filled, one with the unstable polymer solution and the other with nonsolvent, and the two fluids were simultaneously but separately sprayed at about the same flow rate onto a previously cleaned Teflon rotating mandrel. The mandrel rotation speed and carriage movement speed were set at predetermined values, and both nonsolvent and the unstable polymer solution were sprayed at predetermined pressures, angles, and distances between the modified spray gun nozzles and the mandrel. The entire process was carried out, preferably, in a chemical fume hood. The wall thickness of the membrane produced is related to the volume of polymer solution sprayed.

EXAMPLES

Processing Conditions

Various combinations of parameters related to the spraying and phase-inversion techniques can be used to produce the white, opaque, gel-like tubular membranes of the present invention with a range of diameters, wall thicknesses, porosities, and mechanical properties. The rough limits of the ranges over which these process parameters for making the present porous membranes can vary were summarized in Table I, supra and further preferred parameters for various membranes are given in Table II, below. Normally, the present membranes are white, opaque and gel-like.

For the examples described here, two kinds of 1.5 mm ID tubular membranes were prepared: with and without a dense inner polymer layer (skin). Both types had a porous, communicating cell wall structure and an outer porous wall. The skin was produced by first spraying the unstable polymer solution from the nozzle of a single modified spray gun in the absence of a spray of nonsolvent (water) from the other modified spray gun. After this step the deposited polymer was dried for 2 minutes at temperatures varying from 65° C. to 70° C., using a quartz heating rod placed 4 cm below the rotating mandrel. The porous wall was subsequently formed by simultaneously spraying water and the thermodynamically unstable polymer solution from the nozzles of each of the modified spray guns. Turbidity appeared in a 1% Cardiothane 51 ® polymer solution in 2:1 THF/1,4 Dioxane solvent mixture once 20 ml of distilled water had been added to 100 ml of the original solution (5:1 dilution ratio solvent/nonsolvent). A polymer-solvent-nonsolvent system was used displaying a relatively high degree of phase separation but still clear rather than turbid. This was achieved by adding 16.5 ml of distilled water to the original polymer (cardiothane 51) solution, which lowered the polymer concentration in the fabricating solution to 0.86% w/v.

The processing conditions used to fabricate tubular membranes with an inner skin are reported in Table III, below.

TABLE II

| | |
|---|---|
| 1. PU solution concentration (% w/v) | 0.3–2.0 |
| 2. Nonsolvent (water) in the PU solution (% v/v) | 0–20 |
| 3. Gas driving pressure (p.s.i.) | 6–15 |
| 4. PU solution flow rate (ml/min) | 0.5–3.5 |
| 5. Nonsolvent (water) flow rate (ml/min) | 0.5–3.5 |
| 6. Angle between spray gun(s) and mandrel (°) | 70–80 |
| 7. Distance between nozzles and mandrel (mm) | 15–100 |
| 8. Mandrel diameter (mm) | 0.5–0.8 |
| 9. Mandrel rotation speed (rpm) | 100–2000 |
| 10. Carriage movement speed (cm/min) | 10–500 |
| 11. Internal nozzles bore (mm) | 0.2–0.5 |

TABLE III

| Parameters | Inner skin (one gun) | Outer wall (two guns) |
|---|---|---|
| 1. Polymer solution concentration (% w/v) | 1 | 0.86 |
| 2. Nonsolvent (water) in the polymer solution (% v/v) | 0 | 16.5 |
| 3. Gas driving pressure (psi) | 7 | 15 |
| 4. Polymer solution flow rate (ml/min) | 0.5 | 3.5 |
| 5. Nonsolvent (water) flow rate (ml/min) | — | 3.5 |
| 6. Angle between spray gun(s) and mandrel (°) | 75 | 75 |
| 7. Distance between nozzles and mandrel (mm) | 90 | 40 |
| 8. Mandrel diameter (prosthesis ID) (mm) | 1.5 | 1.5 |
| 9. Mandrel rotation speed (rpm) | 600 | 600 |
| 10. Carriage movement speed (cm/min) | 70 | 70 |
| 11. Internal nozzles bore (mm) | 0.3 | 0.3 |
| 12. Length of spary depositon (cm) | 11.5 | 11.5 |
| 13. Volume of polymer solution used (ml) | 3 | 3 |
| 14. Fabricating time (min) | 1.5 | 13.5 |

Figure 2:
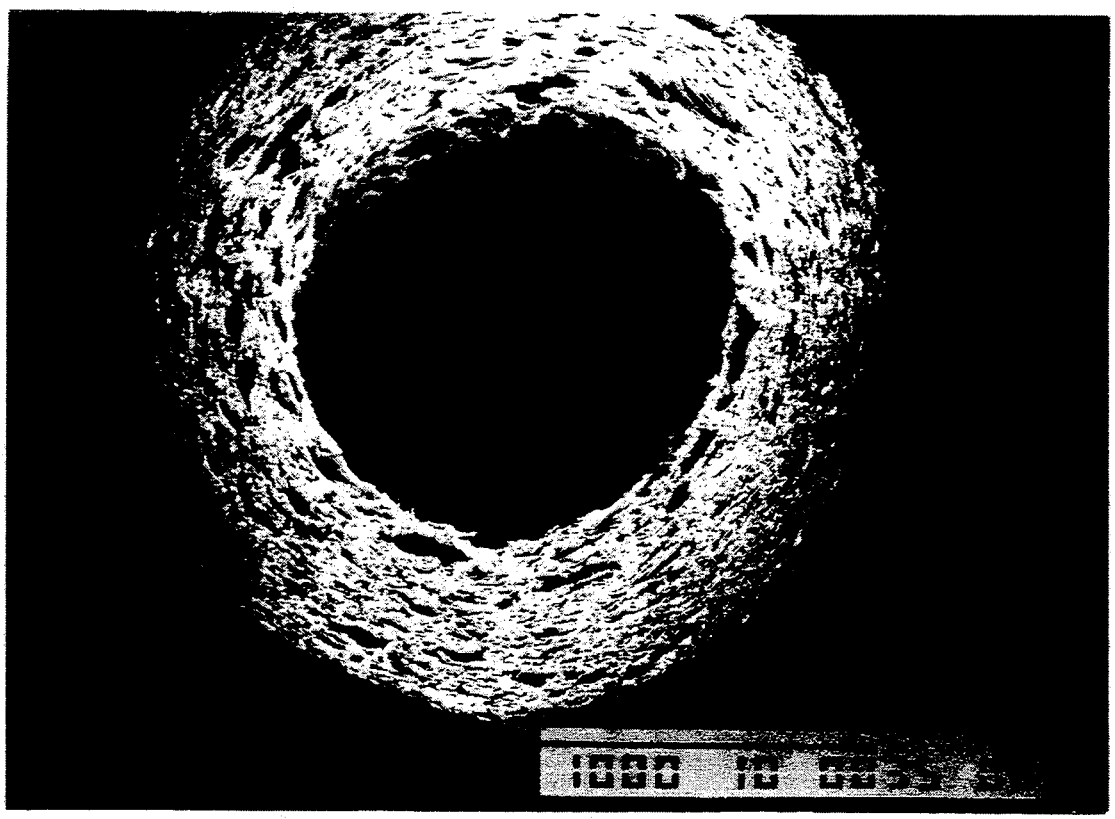
FIGS. 2 and 3 are scanning electron micrographs of a membrane made according to the present invention.
Figure 3:
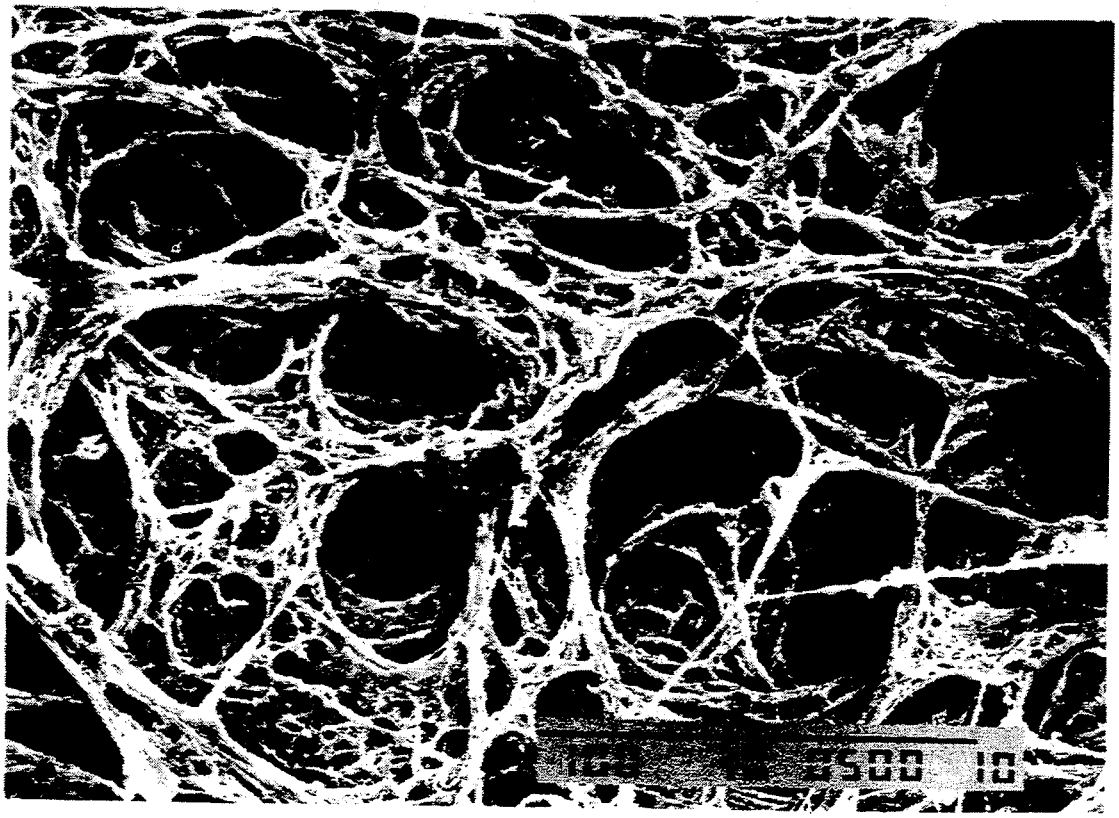

Scanning electron micrographs of a membrane fabricated according to the present invention as embodied in the above examples, are shown in FIGS. 2 and 3. The tubular structure shows a thin (~10 μm) relatively smooth inner skin and a spongy porous wall approximately 400 μm thick with a porous outer surface. The wall is made of circularly oriented layers of polymeric material forming an open-cell porous structure (FIG. 2). At high magnification the outer surface shows a mesh of polymer fibers of approximately 2 μm diameter, with interfiber spaces ranging from 20 to 40 μm, which penetrate into the bulk of the material (FIG. 3).

The membranes exhibited a porosity of approximately 78% and the hydraulic permeability of membranes without inner skin was in the order of 14 ml/min/cm$^2$ at 120 mm Hg.

The present tubular membranes as prepared in the above examples exhibited favorable properties for surgical handling and implantation. The material was easily penetrated with a 70 micron needle and was about as tear-resistant as a human saphenous vein. Grafts from the present membranes were sufficiently pliant to be flexed and folded as required for suture placement, but showed adequate memory to return spontaneously to their original open, cylindrical configuration. This feature afforded visualization of the back walls of the anastomoses and facilitated needle placement. Preclotting was not employed, yet no suture hole bleeding nor leaking through the graft material was observed. Unskinned prostheses displayed a patency rate of 83% and 50% at 4 and 8 weeks post-implantation in animals respectively. At retrieval time none of these grafts showed any aneurysm formation, perigraft hematomas or rupture. All anastomoses were intact. The grafts moved freely, and external tissue reaction was minimal. Gross examination of patent grafts revealed an inner surface lined with a smooth, thin layer of transparent glistening tissue, with occasional small foci of yellow-tan staining, but no evidence of adherent thrombus or exposed polymer.

Four components of the graft healing response were examined by light or electron microscopy. (1) the luminal lining, (2) the graft material, (3) the inflammatory reaction, and (4) the incorporation of native tissue.

The major portion of the internal capsule of the 4-week grafts was composed of a thin tissue membrane which at higher magnification was found to be made of a single layer of endothelial-like cells overlying several layers of myofibroblastic cells. In other regions exhibiting a less mature surface, the luminal lining was composed of isolated cells situated within a fibrin protein matrix. The internal capsule of the 8-week grafts showed a multilayered collagenous structure almost completely lined with endothelial-like cells overlying multiple layers of myofibroblastic cells. The mean internal capsule thickness was 7.3±6.9 μm for the 4-week grafts; 32.9±19.6 μm for the 8-week grafts. Under SEM examination the endothelial-like cells appeared as flattened cells with elongated nuclei.

The polymeric material seemed to be relatively resistant to biodegradation and tissue processing and was visible as a refractile substance distributed throughout the wall of the conduit. Its birefringence to polarized light remained undiminished at 8 weeks compared to the appearance at four weeks.

In the 4-week grafts, isolated histiocytic cells were present within the graft material voids as well as adjacent to the external aspect of the prosthesis. These cells occasionally fused to form "small" giant cells. A localization of the inflammatory response to the external surface of the prostheses at both time periods was also noted. The process of external organization formed a capsule with an indistinct line of demarcation from the region which contained the polymer. Its external aspect was clearly separated from the adjacent tissue.

In addition to the histiocytic infiltration of the graft material voids, fibrinous protein and individual fibroblastic cells were also present in the 4-week samples, with evidence of early collagen deposition. In the 8 week samples small islands of vascularized, organized collagenous tissue were seen in the polymer voids. The development of a mature stable luminal interface and the deposition of collagenous tissue within the grafts was well advanced by 8 weeks. Apparently, this healing process did not occur at the expense of luminal cross-sectional area, nor did it materially affect mural thickness. The mean total wall thickness (internal capsule plus polymer region plus external capsule) was 232±57 at 4 weeks, and 274±128 μm at 8 weeks.

It is possible to incorporate bioactive materials into the tubular membranes of the present invention. The bioactive material can be slowly released from the membrane to promote healing at the implant site or released from the membrane into the system of the implantee to be effective at the site where the bioactive material is needed. Bioactive polypeptides, anticoagulants and other growth stimulating or inhibiting factors, for example, can be incorporated into the present gel-like tubular membranes. This can be achieved by dissolving the bioactive material in the nonsolvent and forming the tubular membrane using the present spray-phase inversion process wherein the nonsolvent contains the bioactive materials. Using this approach, it may be feasible to prepare synthetic small-diameter vascular prostheses, that are porous, distensible, tubular membranes which incorporate albumin and basic Fibroblast Growth Factor (bFGF) to achieve a slow, local release which could influence the healing process. Experiments have demonstrated that albumin and bFGF can be released at an approximately constant rate for at least 2 weeks and that the bFGF initially incorporated in the membrane remained biologically active as shown by in vitro proliferation of human endothelial cells.

I claim:

1. A porous polymeric membrane wherein said membrane is elasotomeric, biocompatible and blood compatible and which has a spongy porous cell wall structure with a filamentous outer surface with interfiber spacing ranging from about 30 to 150 microns and a filamentous inner surface with an interfiber spacing ranging from about 30 to about 150 microns said membrane being prepared by a process comprising the steps of, a) forming a solution of a polymer in a solvent for the polymer;

b) adding a nonsolvent to the polymer solution until a thermodynamically unstable polymer solution is obtained;

c) separately spraying the unstable polymer solution and nonsolvent from separate spray means onto a sliding and rotating mandrel means to form a precipitated material; and d) placing the precipitated material into a bath of nonsolvent to cure the precipitated material.

2. A porous membrane according to claim 1, wherein the polymer is a polyamino-acid, a polysaccharide, a cellulose derivative, an alginate, a silicone, a polyurethane or mixtures thereof.

3. A porous membrane according to claim 1, wherein the solvent is water-miscible and has a low boiling point.

4. A porous membrane according to claim 3, wherein the solvent is tetrahydrofuran, an amide solvent, a sulfoxide solvent, a dioxane or mixtures thereof.

5. A porous membrane according to claim 1, wherein the nonsolvent is miscible with the solvent and has a solubility parameter different from the polymer.

6. A porous membrane according to claim 1, wherein the nonsolvent is water, an alcohol, or water containing a substance which enhances the inducement of solution instability and/or precipitation of polymer from the solution.

7. A porous membrane according to claim 6, wherein the solvent is water, a lower alkanol or mixtures thereof.

8. A porous membrane according to claim 1, wherein the polymer is polyurethane.

9. A porous membrane according to claim 1, wherein the polymer is a polyether urethane-poly(dialkylsiloxane).

10. A porous membrane according to claim 9, wherein the solvent is a mixture of tetrahydrofuran and 1, 4-dioxane.

11. A porous membrane according to claim 10, wherein the nonsolvent is water.

12. A porous membrane according to claim 11, wherein the polymer solution concentration (% w/v) is from about 0.1 to 5.0, the amount of nonsolvent added to the polymer is about 1 to 50 (% v/v), the spray means is driven under gas driving pressure of from about 1 to 45 psi, the polymer solution flow rate from the spray means is about 0.5 to 5.0 ml/min, the nonsolvent flow rate from the spray means is about 0.5 to 5.0 ml/min, the angle between the separate spray means for the nonsolvent and polymer solution and the mandrel means is about 70° to 80°, the distance between nozzles of the separate spray means and the mandrel means of about 15 to 100 mm, the mandrel means diameter is from about 0.5 to 1000 mm, the speed of rotation of the mandrel means is about 100 to 2000 rpm and the sliding movement speed of the mandrel means is about 10 to 500 m/min.

13. A porous membrane according to claim 1 wherein the filamentous inner surface interfiber spacing ranges from about 50 to 150 μm and the filamentous outer surface interfiber spacing ranges from about 50 to 150 μm.

14. A porous membrane according to claim 13, wherein the filamentous inner surface interfiber spacing ranges from about 90 to 150 μm and the filamentous outer surface interfiber spacing ranges from about 90 to 150 μm to 150 μm.

15. A porous membrane according to claim 1, wherein the membrane has a hydraulic permeability measured collecting, in the first minute, of from 30 to 60 ml min-1 cm-2 and a high water content.

* * * * *